(12) United States Patent
Jacob et al.

(10) Patent No.: US 10,631,801 B2
(45) Date of Patent: Apr. 28, 2020

(54) SCINTILLATOR SEALING FOR SOLID STATE X-RAY DETECTOR

(71) Applicant: General Electric Company, Schenectady, NY (US)

(72) Inventors: Biju Jacob, Niskayuna, NY (US); Nicholas Konkle, Sussex, WI (US); Douglas Albagli, Clifton Park, NY (US); William Andrew Hennessy, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 216 days.

(21) Appl. No.: 15/354,820

(22) Filed: Nov. 17, 2016

(65) Prior Publication Data
US 2018/0132805 A1    May 17, 2018

(51) Int. Cl.
*A61B 6/00* (2006.01)
*G01T 1/24* (2006.01)
*H01L 27/146* (2006.01)

(52) U.S. Cl.
CPC .......... *A61B 6/4208* (2013.01); *G01T 1/244* (2013.01); *H01L 27/14634* (2013.01); *H01L 27/14663* (2013.01)

(58) Field of Classification Search
CPC ......... G01T 1/2018; G01T 1/24; G01T 1/244; G01T 7/00
See application file for complete search history.

(56) References Cited

U.S. PATENT DOCUMENTS

| 5,274,237 | A  | 12/1993 | Gallagher et al. |
| 5,641,984 | A  | 6/1997  | Aftergut et al.  |
| 6,642,524 | B2 | 11/2003 | Vafi et al.      |
| 6,927,379 | B2 | 8/2005  | Hoffman          |
| 7,126,130 | B2 | 10/2006 | Hennessy et al.  |
| 7,473,903 | B2 | 1/2009  | DeJule et al.    |

(Continued)

FOREIGN PATENT DOCUMENTS

| JP | 2012-047627 A | 3/2012  |
| WO | 02/37138 A1   | 5/2002  |
| WO | 2008147135 A1 | 12/2008 |

OTHER PUBLICATIONS

"Home: PAVE Technology," PAVE Technology Website, Available Online at http://www.pavetechnologyco.com/html/home.html, Available as Early as Dec. 8, 2004, Retrieved Nov. 18, 2016, 2 pages.

(Continued)

*Primary Examiner* — Dani Fox
(74) *Attorney, Agent, or Firm* — McCoy Russell LLP

(57) ABSTRACT

An x-ray detector comprises: a housing, including a cover fastened on a flange of a flanged base and forming a semi-hermetic seal therebetween, the flanged base including a bottom surface and the flange surrounding a perimeter of the bottom surface; and an x-ray imager positioned on the bottom surface, the x-ray imager including a wireless transmitter, wherein the seal semi-hermetically encloses the x-ray imager in the housing, and is positioned nonadjacently to surfaces in contact with the x-ray imager. In this way, a simpler and less costly seal for a digital x-ray panel can be provide; furthermore, the seal is reusable and resealable, facilitating repair and refurbishment of the device.

20 Claims, 9 Drawing Sheets

(56) References Cited

U.S. PATENT DOCUMENTS

| | | | |
|---|---|---|---|
| 8,415,628 B1 | 4/2013 | Shaw et al. | |
| 2007/0114429 A1* | 5/2007 | Bhadare | G01T 1/244 |
| | | | 250/370.09 |
| 2014/0226795 A1 | 8/2014 | Kitano | |
| 2014/0252229 A1 | 9/2014 | Kondo | |
| 2015/0008330 A1 | 1/2015 | MacLaughlin et al. | |
| 2015/0293237 A1 | 10/2015 | Suzuki et al. | |

OTHER PUBLICATIONS

"PAVE-Flex® Flat Cable Hermetic Seals Product Listing Index," Pave Technology Website, Available Online at http://www.pavetechnologyco.com/design/flex_productindex.html, Available as Early as Oct. 13, 2005, Retrieved Nov. 18, 2016, 2 pages.

Jacob, B. et al., "Radiation Detector Assembly," U.S. Appl. No. 141985,739, filed Dec. 31, 2015, 30 pages.

Jacob, B. et al., "Radiation Detector Assembly," U.S. Appl. No. 14/985,785, filed Dec. 31, 2015, 31 pages.

Jacob, B. et al., "Scintillator Sealing for Solid State X-Ray Detector," U.S. Appl. No. 15/354,760, filed Nov. 17, 2016, 48 pages.

Konkle, N. et al., "Scintillator Sealing for Solid State X-Ray Detector," U.S. Appl. No. 15/358,352, filed Nov. 22, 2016, 44 pages.

International Search Report and Written Opinion issued in connection with corresponding PCT Application No. PCT/US2017/061811 dated Feb. 27, 2018.

\* cited by examiner

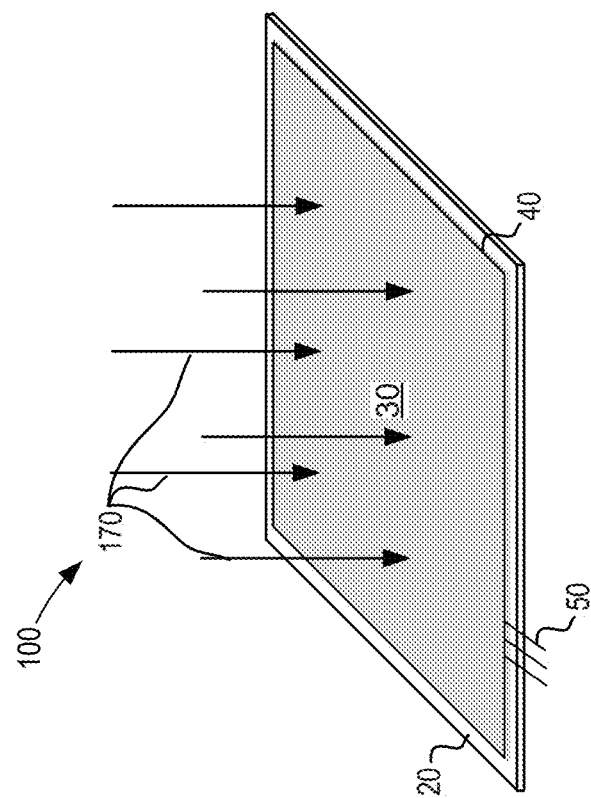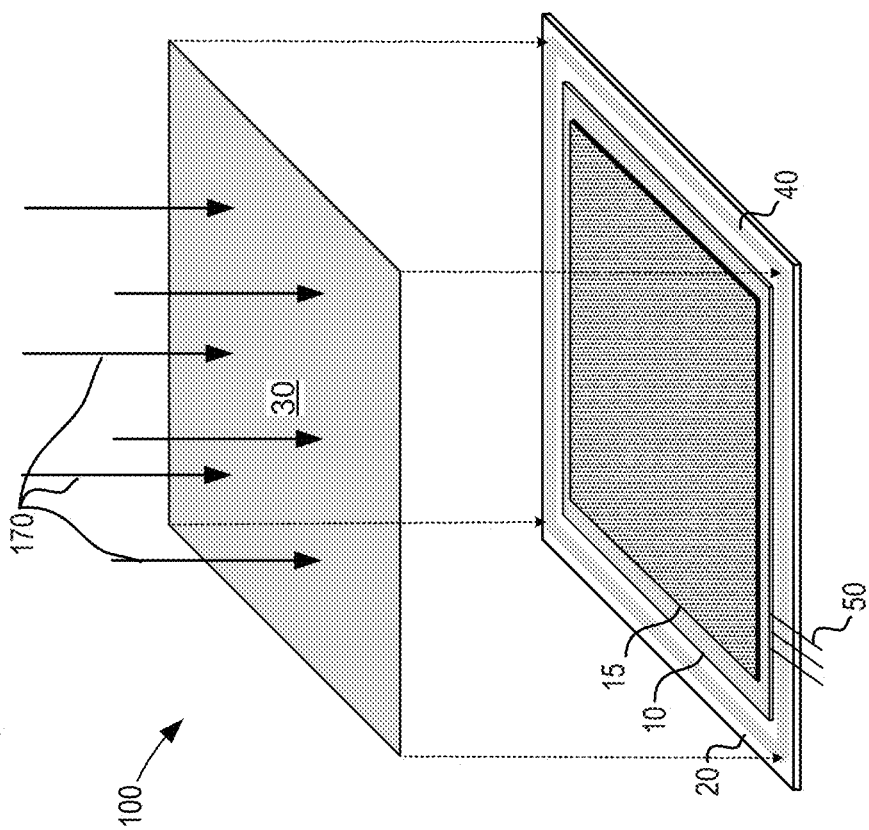

_US 10,631,801 B2_

SCINTILLATOR SEALING FOR SOLID STATE X-RAY DETECTOR

FIELD

Embodiments of the subject matter disclosed herein relate to a solid state x-ray detector. Other embodiments relate to a solid state x-ray detector system and methods of assembling an x-ray detector.

BACKGROUND

X-ray detectors are used in medical diagnostic imaging, medical therapy, and various medical testing and material analysis industries. A common type of x-ray detector uses scintillator materials to convert x-ray photons into visible-spectrum photons as part of the energy detection process, and solid state electronics to convert the visible light photons into digital signals. Scintillator materials can have an affinity to absorb moisture, and solid state electronics may corrode in the presence of moisture, both of which can adversely affect the structure of the scintillator and degrade the image quality of the image detector.

In one embodiment Dejule et al. (U.S. Pat. No. 7,473,903) describe a digital x-ray panel including an x-ray detector formed on a detector substrate, a dam formed on the detector substrate circumscribing the detector matrix, a scintillator material formed on the detector matrix, and a hermetic layer formed on the scintillator material extending on to the surface of the dam. The hermetic layer is deposited as a thin film or coating in an active detector area over the scintillator and detector matrix, encapsulating and hermetically sealing them therein. In other embodiments, additional hermetic seals are provided at a chest wall side of the digital x-ray panel comprising bonding adhesive sealant between an edge of the hermetic layer and a sidewall, and bonding adhesive sealant between an edge of the hermetic layer and an end channel. In another embodiment, an additional hermetic seal is provided comprising bonding adhesive sealant to seal a gap between a protective cover and the hermetic layer.

The inventors herein have recognized various issues with the above approach. Namely, forming a hermetic seal as a coating or thin film on the scintillator requires film deposition equipment which can increase manufacturing time and costs. Furthermore, because of its proximity to the active layers of the x-ray detector, forming the hermetic seal coating or thin film can damage the scintillator, detector matrix, or solid state electronics of the digital x-ray panel. Further still, forming a seal over the active detector area can interfere with the performance of the digital x-ray panel since incident x-rays must be transmitted through the seal prior to reaching the scintillator. Further still, providing multiple hermetic seals within an x-ray detector increases manufacturing complexity and costs. Further still, hermetic seals formed with thin film coatings and bonded adhesive sealant are not removable and resealable, rendering repair and refurbishing of the x-ray panel more difficult and costly. Further still, the x-ray detector includes wired connections for transmitting power and other electrical signals external to the x-ray detector, and these wired connections require further sealing to preserve the hermeticity of the x-ray detector.

BRIEF DESCRIPTION

In one embodiment, the issues described above may be at least partially addressed by an x-ray detector, comprising: a housing, including a cover fastened on a flange of a flanged base and forming a seal therebetween, the flanged base including a bottom surface and the flange surrounding a perimeter of the bottom surface; and an x-ray imager positioned on the bottom surface, the x-ray imager including a wireless transmitter, wherein the seal semi-hermetically encloses the x-ray imager in the housing, and is positioned nonadjacently to surfaces in contact with the x-ray imager.

In another embodiment, an x-ray imaging system comprises a housing, including a cover fastened on a raised flange of a flanged base thereby forming a seal therebetween, an x-ray imager positioned on a bottom surface of the flanged base inside the housing below and nonadjacent to the seal, the raised flange surrounding a perimeter of the bottom surface, a wireless transmitter positioned inside the housing and conductively coupled to the x-ray imager, and a wireless power source positioned external to the housing.

In another embodiment, a method of assembling an x-ray detector including an x-ray imager, a housing, and a wireless transmitter, comprises positioning the x-ray imager on a bottom surface of the housing, the housing comprising a cover and a raised flange surrounding a perimeter of the bottom surface, positioning the wireless transmitter inside the housing and conductively coupling the wireless transmitter to the x-ray imager, and sealing the x-ray imager within the housing, including affixing the cover on a top surface of the raised flange to form a seal between the cover and the raised flange, wherein the seal is positioned outside of a path of x-rays incident at the x-ray imager.

In this way, the technical effect of providing a seal for a digital x-ray panel in a simple, low cost way can be achieved. Further technical effects are listed as follows. In the case where the seal is reusable and resealable, the technical effect of enabling repair and refurbishment of the device is facilitated. Further still, the seal is positioned away from the detector-active region and thus does not interfere with the detector operation, and reduces a risk of damaging the detector components during manufacturing. Further still, positioning the seal away from the detector-active region can facilitate addition of other components within the x-ray detector housing such as getter material, sensors, electrical connectors, and the like, which can increase the performance and functionality of the x-ray detector. Further still, the seal facilitates sealing multiply-tiled large image array detectors within a single x-ray detector. Further still, the seal may comprise a semi-hermetic seal or a hermetic seal. Further still, the hermeticity of the sealing of the x-ray panel is increased because transmission of power and other digital signals across the housing of the x-ray panel is performed wirelessly and sealing around wired connectors entering the housing is precluded.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 1A and 1B are schematics showing perspective views of an x-ray detector with a seal bonded at the detector substrate surface.

DETAILED DESCRIPTION

The following description relates to various embodiments of an x-ray detector, an x-ray detector system, and a method for assembling an x-ray detector.

In one embodiment, the issues described above may be at least partially addressed by an x-ray detector, comprising: a housing, including a cover fastened on a flange of a flanged base and forming a seal therebetween, the flanged base including a bottom surface and the flange surrounding a perimeter of the bottom surface; and an x-ray imager positioned on the bottom surface, the x-ray imager including a scintillator and an image sensor, wherein the seal may semi-hermetically enclose the x-ray imager in the housing, and may be positioned nonadjacently to surfaces in contact with the x-ray imager.

X-ray detectors use scintillator materials to convert x-ray photons into visible-spectrum photons as part of the energy detection process. The detector is sealed to prevent moisture from being absorbed into the scintillator, as moisture can adversely affect the crystal structure of the scintillator materials and degrade the image quality of the image detector. The solid state electronics, which convert the visible-spectrum photons to electrical signals in the image detector should also be protected from moisture to prevent their corrosion and consequent performance degradation. Current methods used to hermetically seal x-ray detectors include using an epoxy sealant to bond a cover to the top layer of the image detector or the image detector substrate, as shown in FIG. 1. Bonding the cover to the image detector to hermetically seal the x-ray detector can increase a risk of damaging the image detector due to the proximity of the seal to the image detector components; also, a non-resealable seal such as an epoxy bond can render repairs unworkable and costly since breaking the seal can damage the detector.

Figure 2B:
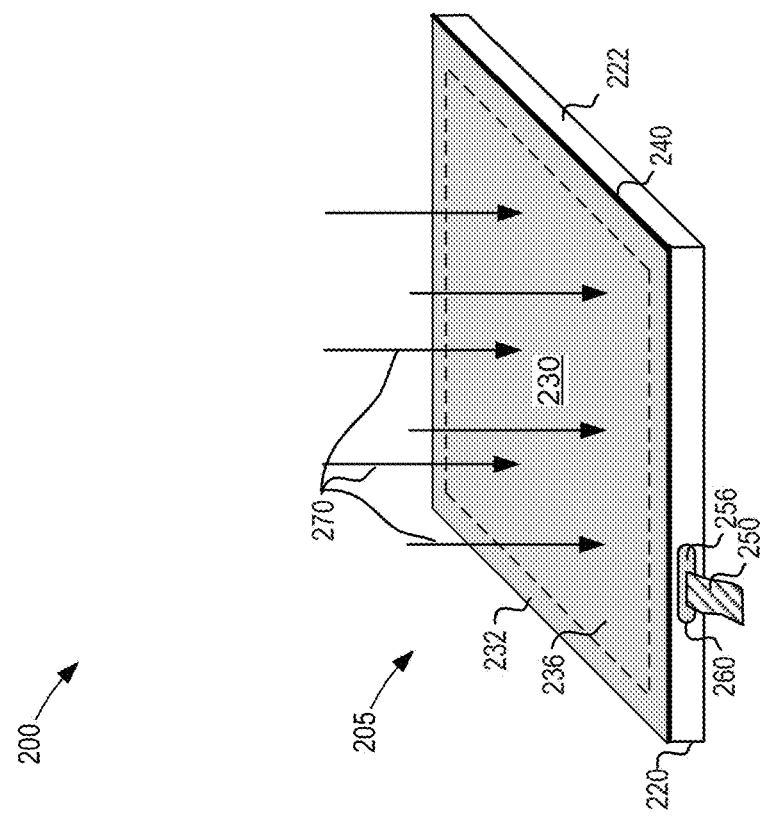
FIGS. 2A and 2B are schematics showing perspective views of wired x-ray detector including a seal.
Figure 2A:
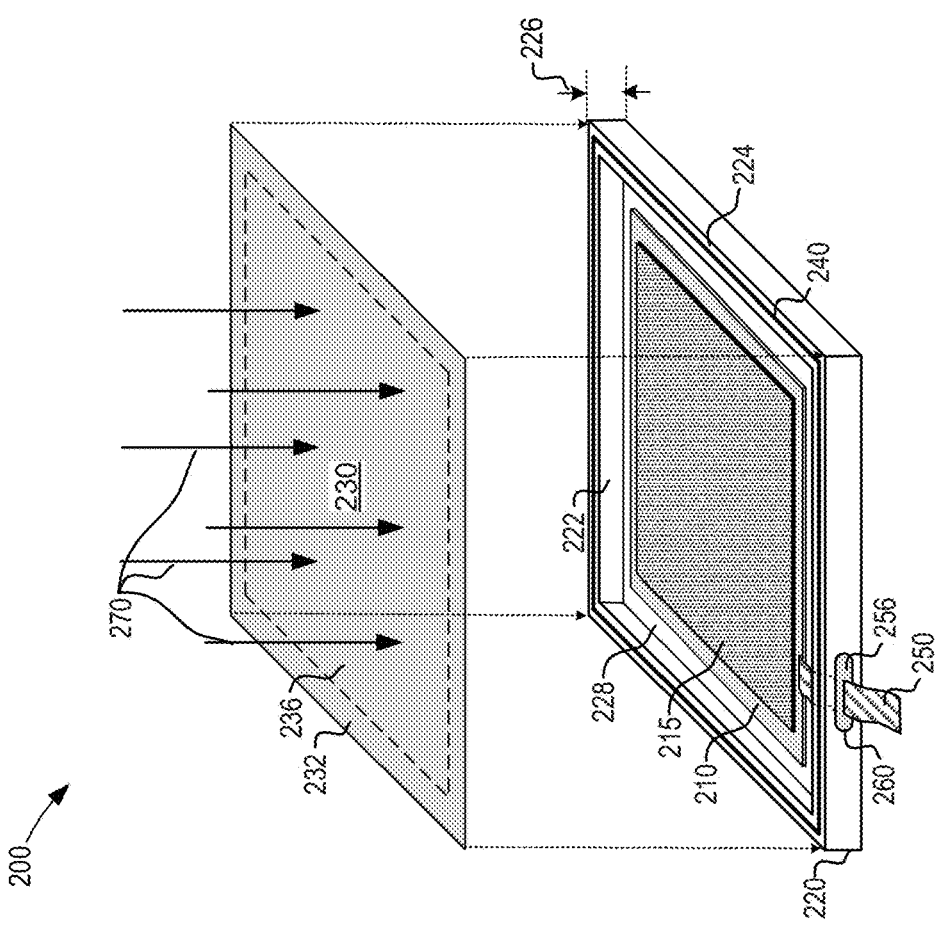
Figure 4:
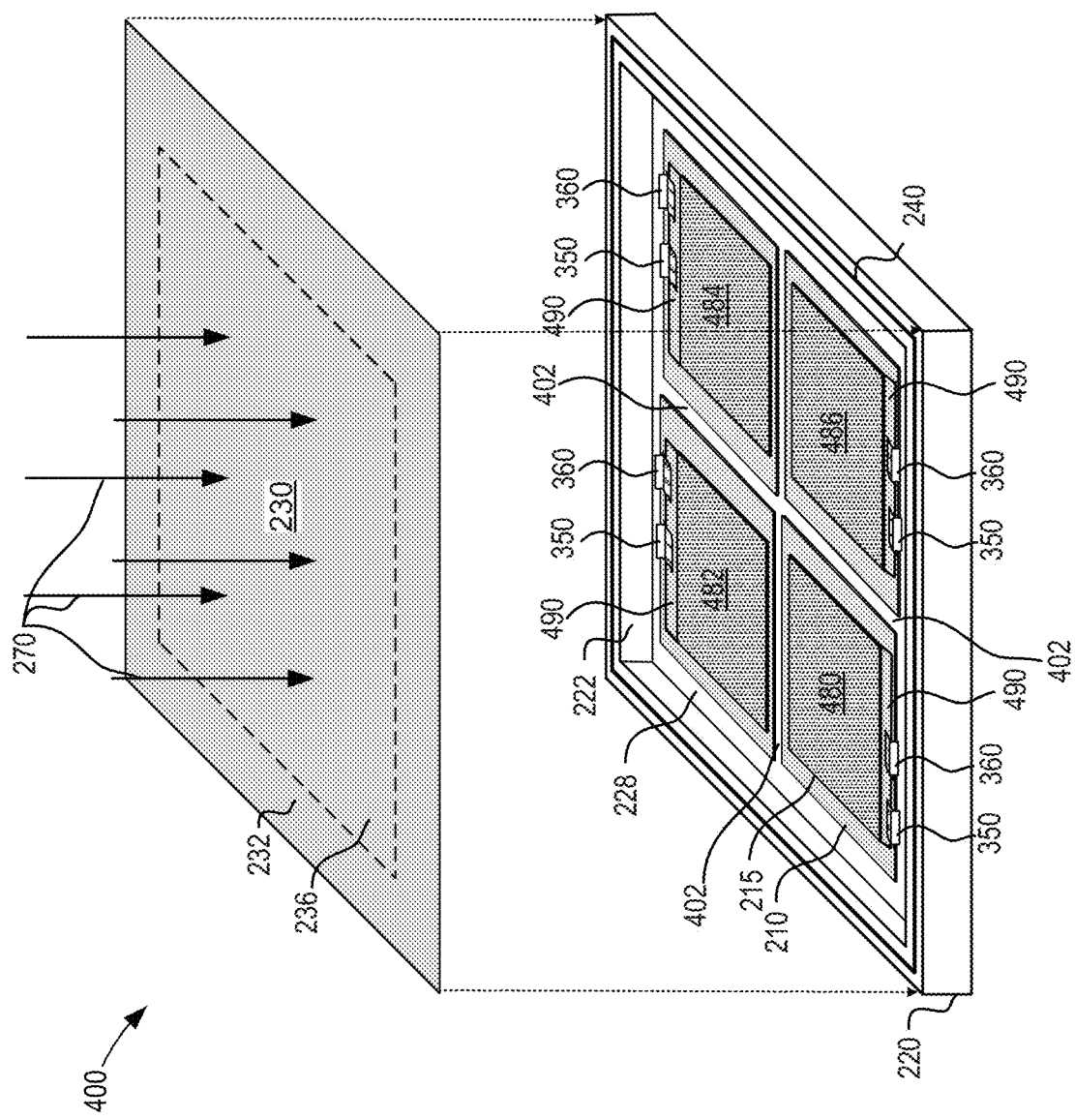
FIG. 4 is a schematic showing a perspective view of a wireless x-ray detector including tiled x-ray imagers and a seal.
Figure 7:
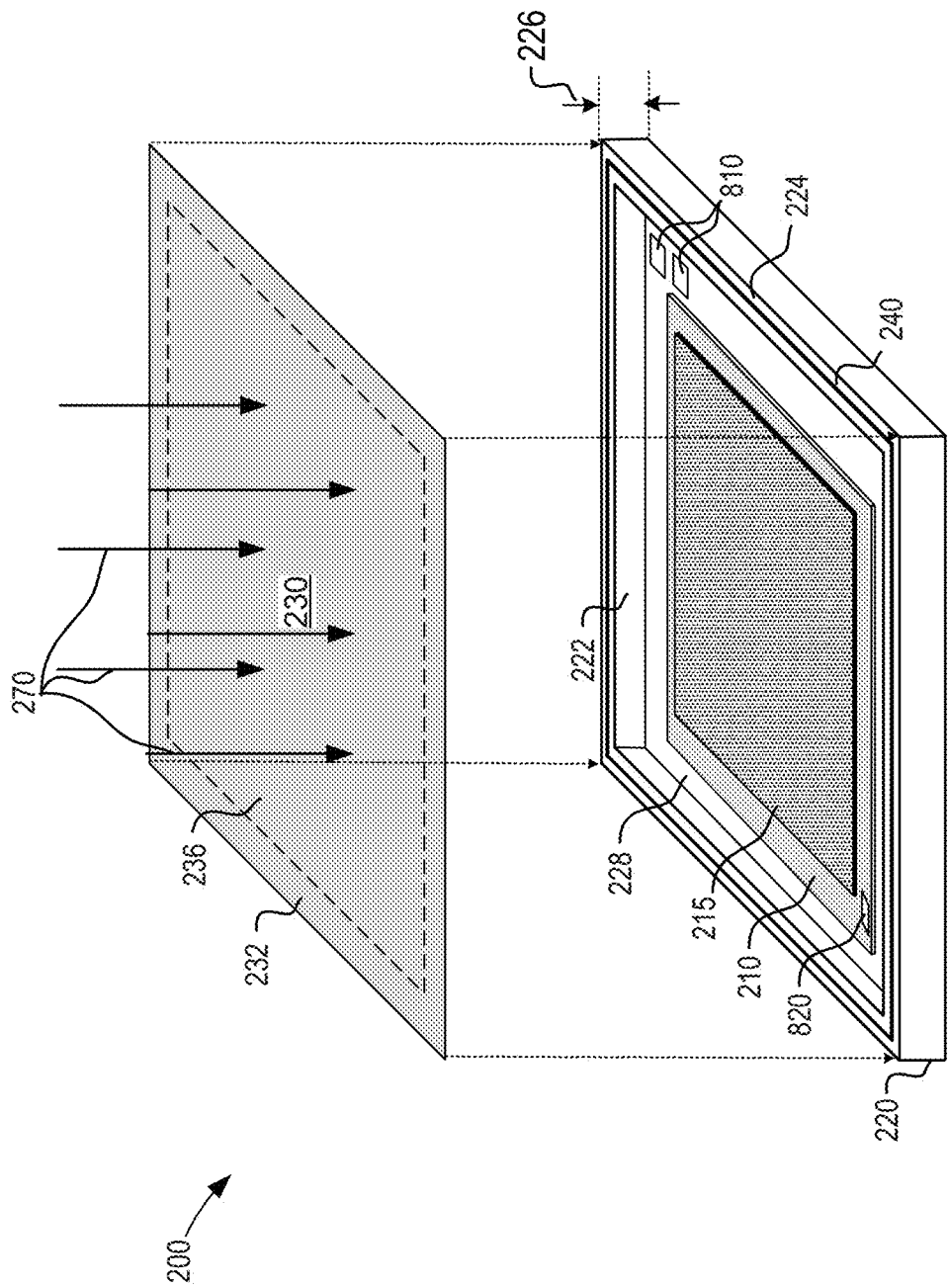
FIG. 7 is a schematic showing an expanded perspective view of a wireless x-ray detector including a seal.
Figure 8:
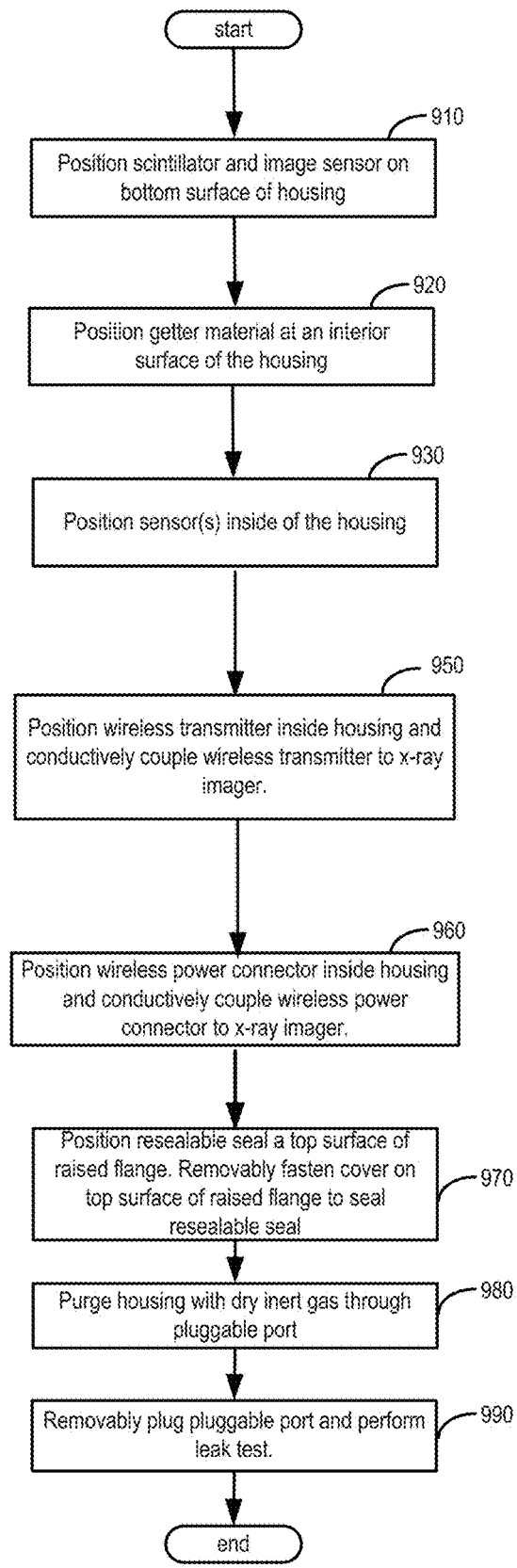
FIG. 8 is an example flow chart for a method of assembling the wireless x-ray detectors of FIGS. 3A, 3B, 4, 5, and 7.
Figure 9:
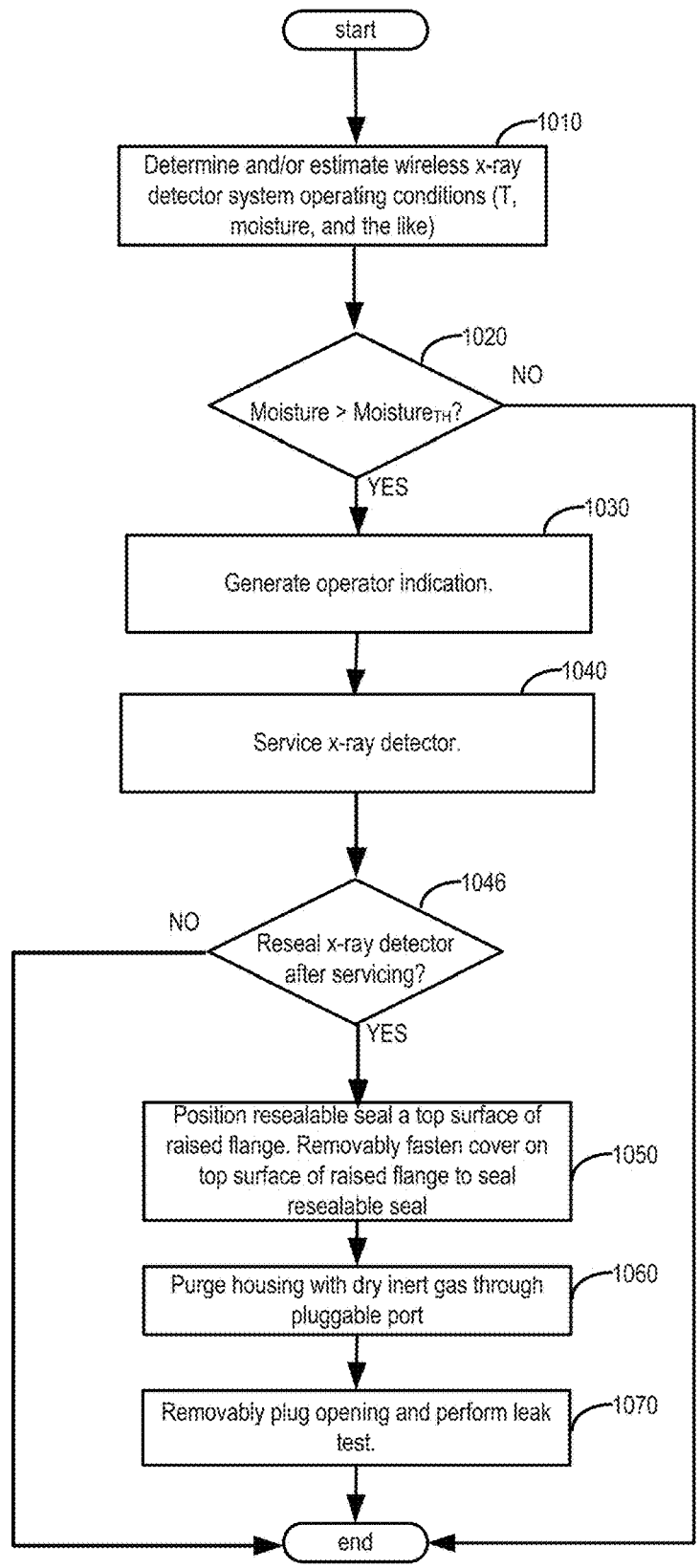
FIG. 9 is an example flow chart for a method of resealing the wireless x-ray detectors of FIGS. 3A, 3B, 4, 5, and 7.

Accordingly, an improved x-ray detector including a seal is shown in FIGS. 2A and 2B. In some embodiments, the seal may be resealable, while in other embodiments, the seal may be non-resealable. The seal may be used for sealing large image array x-ray detectors configured with multiply-tiled Complementary Metal Oxide Semiconductor (CMOS) detectors, as shown in FIG. 4. The seal can be configured in various ways as shown by FIGS. 5, and 6A-6C. The x-ray detector configuration with the resealable seal also facilitates addition of getter material, sensors, and other components (as shown in FIG. 7) within the x-ray detector that can increase detector performance and/or life. The resealable seal also aids in simplifying x-ray detector assembly methods, and x-ray resealing methods, as shown in FIGS. 8 and 9.

Turning now to FIGS. 1A and 1B, they illustrate a schematic of a flat panel x-ray detector 100 having a non-resealable bonded adhesive seal 40. FIG. 1A illustrates a partially exploded view of the x-ray detector 100 with its cover 30 raised above the x-ray imager, the x-ray imager comprising the scintillator 15 and the image detector 10 layers. Incident x-rays 170 are directed through the cover 30 of the x-ray detector 100 where they are absorbed by the scintillator layer 15 and converted to visible light photons. Some examples of scintillator materials include ionic salts such as cesium iodide (CsI), a hygroscopic, crystalline material, with needle-shaped crystals. CsI crystals are oriented perpendicular to the plane of an adjacent (e.g., glass) substrate 20 and act as short optical fibers to ensure that visible light photons originating in a crystal preferentially exit the crystal at its end and into an adjacent corresponding photodetector, rather than propagating among adjacent crystals within the CsI layer. The visible light photons exiting the scintillator material are sensed by the image detector 10, which converts and outputs them as digital signals from the detector via connectors 50. The output digital signals are then input into a computer processor, where they are processed into an image for display.

Current methods used to seal x-ray detectors vary depending on the type of image sensor. In an amorphous silicon-based imager as shown in FIG. 1, the scintillator (CsI) is usually grown on the glass thin film transistor (TFT) panel. The x-ray detector housing cover 30 is bonded to the glass detector substrate 20 with an epoxy seal 40, providing a semi-hermetic barrier at each edge of the cover 30, as shown in FIG. 1B. In a CMOS (Complementary Metal Oxide Semiconductor) based image sensor the scintillator is usually grown on a different substrate (e.g., fiber optic plate) and the seal is achieved by coating the exposed area with organic materials that provide moisture barrier like parylene. Organic materials, such as epoxy adhesives, sealants, and coatings, do not provide hermeticity, but rather offer a low diffusion rate of moisture, the diffusion rate being dependent upon the morphology of the seal, the path length required for moisture to penetrate through diffusion, and the quality of their adhesion to the surfaces they are sealing. In some cases, epoxy or other organic adhesive sealants are provided in addition to the coatings to augment the seal path length, thereby increasing the moisture diffusion time through the seal. Epoxy sealants, adhesives, and organic coatings are thus semi-hermetic seals.

Both the epoxy seal and the coating seal approaches are non-resealable seals that are formed directly on the x-ray detector scintillator, image detector, and/or substrate layers in contact therewith. Forming a non-resealable seal as a coating or thin film on the scintillator requires film deposition equipment which can increase manufacturing time and costs. Furthermore, because of its proximity to the active layers of the x-ray detector, forming the seal, coating, or thin film can damage the scintillator, detector matrix, or solid state electronics of the digital x-ray panel. Further still, forming a seal over the active detector area can interfere with the performance of the digital x-ray panel since incident x-rays 170 must be transmitted through the seal prior to reaching the scintillator. Further still, providing multiple seals within an x-ray detector increases manufacturing complexity and costs. Further still, seals formed as thin film coatings or bonded adhesive are not removable and resealable, rendering repair and refurbishing of the x-ray panel more difficult and costly.

The evolution of digital x-ray detectors has included the development of CMOS (Complementary Metal Oxide Semiconductor) based digital x-ray detectors. Digital CMOS x-ray detectors are drawing more attention and becoming more popular in the area of fluoroscopic x-ray imaging especially in surgical and interventional applications because they exhibit extremely low electronic noise. These solid state electronic components should also be protected from moisture to prevent their corrosion and consequent performance degradation. CMOS imagers further comprise large active image areas required for radiography applications are realized by tiling multiple sensors into a larger sensor panel. Large-pixel tile array CMOS detector technology is well-suited for use in radiological-imaging applications because it is manufacturable in large areas, meets or surpasses radiological performance requirements, and offers digital-imaging system design flexibility not available from other radiological-imaging technologies. However, these large tile array imagers are more challenging for conventional semi-hermetic scintillator seals, such as adhesive and coating sealants formed on the surfaces of the tiled components and substrates, because the surface topology of a multi tile-array is much more complex than that for a single tile. For example, tiled imagers have seams between the tiles and water can find its way into the seams. Furthermore, tiled imagers do not have a continuous substrate surface on which a seal can be applied to a cover, rendering it more difficult for coating and thin film type seals to prevent moisture intrusion and degradation of the tiles.

Reference will be made below to exemplary embodiments of the inventive subject matter, examples of which are illustrated in the accompanying drawings. Wherever possible, the same reference numerals used throughout the drawings refer to the same or like parts.

Turning now to FIGS. 2A and 2B, they illustrate an embodiment of an x-ray detector 200, including a seal 240 for sealing a scintillator 215 and an image sensor 210 inside a housing. The housing comprises a cover 230 and a flanged bathtub-structured base with a bottom surface 228 and a raised flange 220 surrounding the perimeter of the bottom surface 228. In FIGS. 2A and 2B, the bathtub housing is rectangular in geometry, however in other embodiments, the shape of the bathtub housing can take on other geometries such as circular, triangular, polygonal, non-symmetrical shapes, and the like. The cover comprises a central, active region 236 (delineated by the dashed border) through which x-rays 270 are incident into the x-ray detector 200, and a sealing region 232 around the perimeter of the cover 230 where x-rays 270 are non-incident. Accordingly, the sealing region 232 may form a picture frame layout surrounding the active region 236 of the cover 230. Dimensions of active region 236 may correspond to the dimensions of the scintillator 215 and/or image sensor 210 so that essentially all incident x-rays 270 are directed through the cover 230 to the scintillator 215 and image sensor 210. In some examples, the sealing region 232 of the cover may be constructed to be thicker in dimension to provide greater structural strength and rigidity for sealing and attaching the cover to the raised flange 220, while the active region 236 may be constructed to be thinner in dimension to reduce a risk of interference with the incident x-rays 270 to the x-ray detector 200. Similar to the sealing region 232 of the cover 230, the raised flange 220 may comprise a rigid solid material to provide greater structural strength and rigidity for sealing and attaching the cover 230 to the raised flange 220.

The housing may be made from many different types of solids including aluminum, stainless steel, other metals, polymers, combinations thereof, and the like. In one example, the housing may be constructed of a magnesium alloy, to yield a lighter-weight structure. In another example, the housing may be constructed from a carbon fiber composite coated or laminated with a metal coating or sheet to provide increased hermeticity at and in the vicinity of the surfaces of the sealing region 232 and the raised flange 220. The central active region 236 may be constructed from aluminum, although a fiber reinforced composite material having a thin metal coating or sheet covering may also be utilized. The flanged base may be constructed as one continuous piece of the solid material or as several pieces joined together using an attachment that hermetically seals the pieces together.

Each side of the raised flange 220 extends upward from the bottom surface 228 creating a cavity volume for positioning the x-ray detector components such as the scintillator 215 and the image sensor 210. In the non-limiting example depicted in FIGS. 2A and 2B, the housing is generally rectangular having sides that are approximately 90 degrees from the bottom and having a pair of matching parallel sides. In other embodiments the housing may comprise a non-rectangular shape and the walls of the raised flange could extend upward from the bottom surface 228 at a non-perpendicular angle. It should be understood that a person of ordinary skill in the art would understand that the compartment is not limited in its shape or geometry. The seal 240 may be designed to match the shape and geometry and dimension of the sealing surfaces (e.g., the top surface 224 and the sealing region 232) so that a continuous seal can be formed surrounding the perimeter of the raised flange 220. In this sealing design, the seal 240 along with sealing surfaces (e.g., the top surface 224 and the sealing region 232) can all be easily scaled in size and in shape. Furthermore, the housing bottom surface may be the same dimensions as the image sensor 210, or it may be of a larger dimension on one or more sides, leaving portions of the perimeter of the bottom surface 228 uncovered by the image sensor 210, as shown in FIG. 2A. Having portions of the perimeter of the bottom surface 228 uncovered by the image sensor 210 may be helpful for spacing and positioning additional components such as getter material or sensors, and the like, as further discussed hereinafter. Increasing spacing and reducing crowding of components within the housing can aid in reduction of heat accumulation within the housing, thereby reducing a risk of degradation of the x-ray detector.

The housing cover 230 may be shaped to match the dimension and perimeter of the raised flange 220. In some embodiments, the cover 230 may extend slightly beyond the perimeter of the raised flange 220, defining an overlapping lip that can aid in sealing the x-ray detector 200, as discussed hereinafter. The cover 230 may be constructed from a rigid, solid material designed to create a semi-hermetic seal when attached to the raised flange 220, as shown in FIG. 2B. The cover 230 can be a thin sheet of aluminum, another low atomic number metal, a composite structure with laminated metal foils, other metals, a plastic, or any other hermetic material. The cover may be homogeneous in thickness or may vary in thickness to ease manufacture. In some embodiments, the cover 230 may comprise a thinner central active region 236 and a thicker perimeter sealing region 232, as shown in FIG. 2. The thinner central active region 236 may be constructed from a low atomic number (e.g., low density) metal such as aluminum so to reduce any interference with incident x-rays 270 into the x-ray detector. The thicker sealing region 232 may be constructed from a strong, rigid material for maintaining the structural integrity of the cover and for maintaining integrity of the sealing surface contacting the seal 240.

In some embodiments, the seal 240 may comprise a non-resealable seal such as an epoxy seal, adhesive sealant, or a coating seal, as described above. The seal 240 may also comprise other types of non-resealable seals. Non-resealable seals may be unsealed by applying heat, solvents, and combinations thereof. However, in general, unsealing non-resealable seals may destroy the non-resealable seal and a new seal may be applied to reseal the x-ray detector. In other embodiments, the seal 240 may comprise a compressible, homogeneous, sealable material such as a rubberized, polymeric, metallic, or non-metallic gasket. Metallic gaskets may provide for a hermetic resealable seal. A non-metallic gasket may provide a semi-hermetic seal, but may advantageously impart a higher resealability to the seal 240. As a further example, the seal 240 may comprise a composite structure including a non-metallic gasket coated or covered with a metallic coating or sheeting to provide both increased hermeticity and increased resealability. The seal 240 may also comprise a resealable adhesive, however the resealability may depend on the resealability of the adhesive; for example, resealability may decrease due to partial reductions in adhesiveness when the seal is resealed. Furthermore, the seal 240 comprises a continuous member that surrounds the perimeter of the bottom surface 228. As such, when the cover 230 is attached to the raised flange 220, as shown in FIG. 2B, the seal 240 is compressed and sandwiched between sealing region 232 and the top surface 224, thereby sealing the x-ray detector 200. The seal provided by the seal 240 may be a hermetic seal or a semi-hermetic seal, the type of seal depending at least partially on the nature of the material of construction of the seal 240. The sealing region 232 and the top surface 224 along with the seal 240 thus form the sealing surfaces for the x-ray detector. As described above, example materials that can be used for the seal 240 include metallic, non-metallic, and both metallic and non-metallic materials. For example, the seal 240 may be constructed of a metal or a glass, or other ceramic or semiconductor material. A seal 240 constructed of metal or glass may provide a seal having increased hermeticity relative to non-metallic and non-glass seal materials. Some examples of non-metallic resealable seal materials include nitrile rubber, Neoprene, Viton, butyl rubber, and ethylene propylene diene monomer (EPDM) rubber.

The seal 240 may be homogeneous in that it is constructed of a single homogeneous body of material throughout. In other embodiments, the seal 240 may be homogeneous in that it is constructed with a uniform and continuous cross-section throughout. In some examples, the cross-section of the seal 240 may comprise a solid cross-section of material, and in other examples, the seal 240 may comprise a hollow cross-section of material and the hollow cavity within the seal 240 may be evacuated or filled with an inert dry gas. In this way the integrity of the seal 240 may be increased and a risk of moisture intrusion into the x-ray detector is reduced (because there are no breaks or discontinuities in the seal body), as compared to conventional x-ray detector seals comprising a combination of both coatings or thin film layers and epoxy or other bonded seals.

The resealability of the seal 240 may be imparted at least partially by its compressibility. Upon sandwiching the seal 240 between the top surface 224 of the raised flange 220 and the sealing region 232 of the cover 230, the seal 240 is essentially elastically (e.g., reversibly) compressed or deformed, thereby providing a seal therebetween. Thus, when the cover 230 is raised from the top surface 224 of the raised flange 220, the seal 240 rebounds elastically back to its original form, shape, and volume. In this way, the components of the x-ray detector 200 may be serviced, and the seal 240 may be resealed repeatedly by sandwiching the seal 240 between the top surface 224 of the raised flange 220 and the sealing region 232 of the cover 230.

The resealability of the seal 240 may also imparted at least partially because of the surface characteristics of the seal 240. The outer surface of the resealable seal is smooth and continuous enough such that when compressed against the surfaces of the top surface 224 and the sealing region 232 of the cover 230, the region between the seal 240 and those surfaces are sealed continuously with no gaps or discontinuities. In this way, if the surfaces of both the top surface 224 and the sealing region 232 are relatively flat, smooth and rigid, the sealing of the x-ray detector 200 is achieved more easily since the resealable seal can be more homogeneously compressed around the entire perimeter of the raised flange 220. Furthermore, the coefficient of friction between the surface of the seal 240 and the top surface 224 and sealing region 232 should be high enough so that the seal 240 does not slip off either surface when compressed therebetween. In some embodiments, a track or raceway for friction fit-seating the seal 240 at the top surface 224 or the sealing region 232 may be provided to facilitate holding the seal 240 between the top surface 224 and the sealing region 232 during the sealing process.

The resealability of the seal 240 may also imparted at least partially because the seal 240 is held in place non-permanently by friction and/or pressure when the resealable seal is sandwiched between the top surface 224 of the raised flange 220 and the sealing region 232 of the cover 230. As such, the seal 240 is neither bonded nor permanently affixed to any surfaces of the x-ray detector 200, which facilitates removal and unsealing of the seal 240 when the housing of the x-ray detector is opened. Furthermore, because the seal 240 is neither bonded nor permanently affixed to the x-ray detector 200, resealing the seal 240 precludes destroying (or irreversibly altering) and removing the original seal material and reapplying new sealing material in order to reseal the x-ray detector 200, as would be performed in the case of resealing a conventional bonded adhesive sealant or coating type of seal.

The scintillator 215 is positioned on the image sensor 210, and the image sensor 210 is positioned on the bottom surface 228 of the flanged base. As described above with reference to FIG. 1, the scintillator 215 absorbs incident x-rays 270 and converts them to visible light photons. Some examples of scintillator materials include ionic salts such as cesium iodide (CsI), a hygroscopic, crystalline material, with needle-shaped crystals. CsI crystals are oriented perpendicular to the plane of the bottom surface 228 substrate, and act as short optical fibers to ensure that visible light photons originating in a crystal preferentially exit the crystal at its end and into an adjacent corresponding photodetector, rather than propagating among adjacent crystals within the CsI layer. In some embodiments, the scintillator may also include thin layer coatings thereon which may be provided for corrosion protection, encapsulation, reflecting visible light, as a resistive mask during manufacturing, and the like. In all embodiments, the seal 240 is positioned separate and apart from the x-ray imager (e.g., the scintillator and the image sensor). In addition, the seal 240 is positioned separate and apart from any surfaces in contact with the x-ray imager, including any thin layer coatings deposited on the scintillator 215. Accordingly, the sealing region and sealing surfaces of the x-ray detector 200 is moved away from the x-ray detector components, which can reduce manufacturing defects and increase useful life of the x-ray detector.

Furthermore, positioning the seal 240 on the top surface 224 and facilitates sealing x-ray detectors comprising a scintillator that is not formed on a glass substrate. Conventional method of manufacturing x-ray detectors permanently seal the x-ray detector cover to the glass substrate of the scintillator; next, electrical and data access connectors are etched into the glass. By moving the sealing region to between the top surface 224 of the raised flange 220 and the sealing region 232 of the cover 230, the electrical and data communication connectors 250 can be provided via a flex cable conductively coupled to the x-ray imager, and the electrical connectors 250 can be threaded through one or more openings 260 in the housing.

The visible light photons exiting the scintillator 215 are sensed by the image sensor 210, which converts and outputs them as digital signals externally from the x-ray detector 200 via electrical connectors 250. The image sensor 210 may comprise one or several pixels. Each pixel has a light photon sensitive area (e.g. a photodiode) that senses visible spectrum photons entering from the scintillator 215. The pixels convert the visible light, based on presence, absence, and intensity into a computer readable digital signal. The output digital signals are then input into a computer processor, where they are processed into an image for display.

To access these data a high speed digital interface connection is provided, with an electrical connector 250 that is conductively coupled to the image sensor 210 (or a printed circuit board, PCB, in electrical communication with the image sensor 210). In addition to transmitting digital signals externally from the x-ray detector, electrical connector 250 transmits the input signals that control and power the image sensor 210, scintillator 215, and other components housed inside the housing. In one embodiment, the electrical connector 250 can comprise a flexible ribbon cable, comprised of a combination of various individual connectors. The flexible quality, and flat aspect ratio of the electrical connector 250 aids in sealing around the electrical connector 250 as it is passed through the housing, as described below. However, the electrical connector 250 is not limited to flat cable ribbons, and other types of electrical connectors 250 can also be used and sealed using the systems and methods described herein. In the embodiment shown in FIGS. 2A and 2B, a single electrical connector 250 is conductively coupled to the image sensor 210; in other embodiments, multiple electrical connectors 250 may be conductively coupled to the image sensor 210 and passed through one or more sealed openings 260 in the housing. As shown in FIG. 2A, the electrical connector 250 is conductively coupled to the image sensor 210 at a position in the housing near the opening 260 and is threaded directly to the opening 260. In other examples, the location of the opening 260 and the location where the electrical connector 250 is coupled to the image sensor 210 may be farther away from each other than as shown in FIG. 2A, and a portion of the electrical connector 250 may be bundled or coiled adjacent to the inside walls of the raised flange 220 or along an exposed portion of bottom surface 228, so as to avoid interfering with incident x-rays 270 passing through the active region 236 to the scintillator 215.

In one embodiment, the electrical connector 250 may be passed or threaded through an opening 260 in the housing, thereby enabling electrical communication into and out from the housing. As shown in FIG. 2A, the opening 260 may be positioned at the side of the raised flange 220, however in other embodiments, the opening 260 may be positioned elsewhere in the housing, such as in bottom surface 228, or in the cover 230. Positioning the opening 260 in the bottom surface 228 or the raised flange 220 may be advantageous as compared to positioning the opening 260 in the cover 230 so as not to interfere with incident x-rays 270 in the active region 236 of the cover 230. Sealing of opening 260 around the electrical connector 250 can be established by a resealable circumferential seal 256 surrounding a transverse cross-section of the cable. In one embodiment, the circumferential seal 256 can be achieved by a rubberized polymeric, metallic, non-metallic, or combination thereof, gasket surrounding a transverse perimeter of the electrical connector 250. In some examples, the resealable circumferential seal 256 can be bonded to the electrical connector 250, while in other examples, the resealable circumferential seal 256 can be tightly friction fit around the electrical connector 250. In either case, upon compression of the resealable circumferential seal 256, a resealable seal between the resealable circumferential seal 256 and the electrical connector 250 is provided. The hermeticity (semi-hermetic or hermetic) of the seal may be determined by the hermeticity of the material of construction used for the electrical connector 250 and the resealable circumferential seal 256, however both semi-hermetic and hermetic resealable seals can be achieved.

An outer dimension of the resealable circumferential seal 256 may correspond in shape and dimension to the shape and dimension of opening 260. In other examples, the outer dimension of the resealable circumferential seal 256 may be slightly larger in shape and dimension to the shape and dimension of opening 260 so that when the resealable circumferential seal 256 is positioned at or inside the opening 260, the resealable circumferential seal 256 is elastically compressed, thereby providing at least a semi-hermetic resealable seal between the walls of the opening 260 and the resealable circumferential seal 256, and between the resealable circumferential seal 256 and the electrical connector 250. Similar to a resealable embodiment of seal 240, the resealable circumferential seal 256 reverts to its original dimension and elasticity when it is removed from the opening 260. In this way, the resealable circumferential seal 256 is imparted with a resealable quality since the electrical connector 250 and the resealable circumferential seal 256 can be disassembled from the opening 260 without destroying or irreversibly altering the resealable circumferential seal 256. Similar to the seal 240 as described above, the resealability of the resealable circumferential seal 256 may be at least partially imparted by its compressibility, its surface characteristics, its homogeneity in its material of construction, and because it is held in place by friction and/or pressure (and not permanently bonded to a surface of the housing). In further examples, the resealable circumferential seal 256 may comprise a single-lipped or double-lipped groove around its circumference, a thickness of the groove corresponding to a thickness of the opening 260. In this way, the resealable circumferential seal 256 and the sealing thereof may be augmented by a single or double lip on either side of opening 260.

The seal 240 is positioned on the top surface 224 of the raised flange 220 and also surrounds the perimeter of the bottom surface 228, scintillator 215, and image sensor 210.

A height 226 of the raised flange is greater than a combined thickness of the scintillator 215 and image sensor 210, and hence the top surface 224 of the raised flange and the seal 240 are positioned at a horizontal plane above the plane of the scintillator 215. As such, the seal 240 is positioned apart from the scintillator 215 and the image sensor 210, and separated from surfaces in direct contact with the scintillator 215 and the image sensor 210. In contrast with conventional coating or adhesive type x-ray detector seals, the seal 240 is positioned at the enclosure boundary (e.g., raised flange 220) of the housing, instead of in proximity to the scintillator 215 and the image sensor 210 and the bottom surface 228 (detector substrate). Furthermore, by positioning the seal 240 at the raised flange 220 of the housing, the seal 240 is located outside of the path of the incident x-rays 270. As such, the seal 240 does not interfere with or contaminate the x-ray detector imaging performance.

Figure 3B:
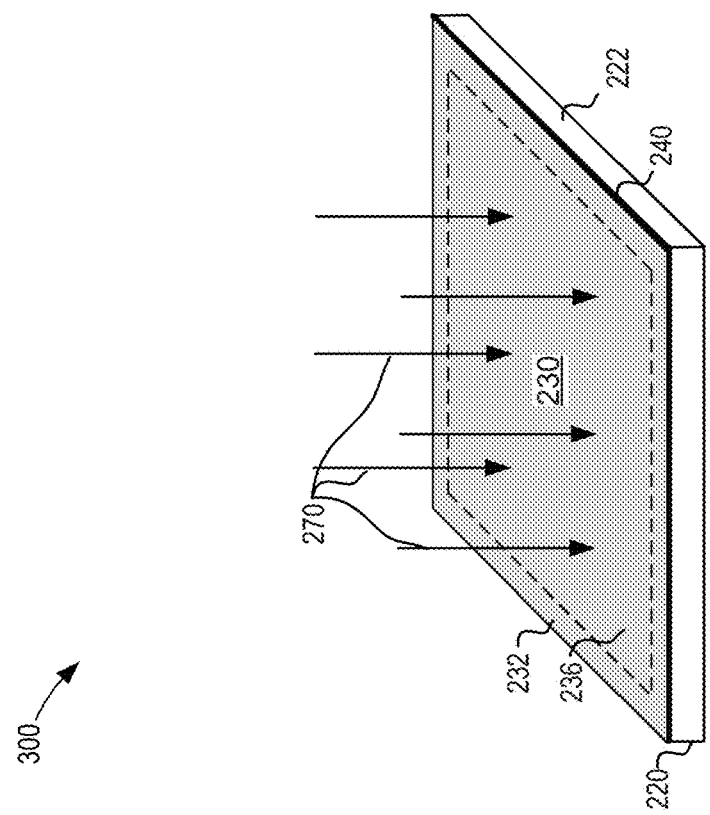
FIGS. 3A and 3B are schematics showing perspective views of a wireless x-ray detector including a seal.
Figure 3A:
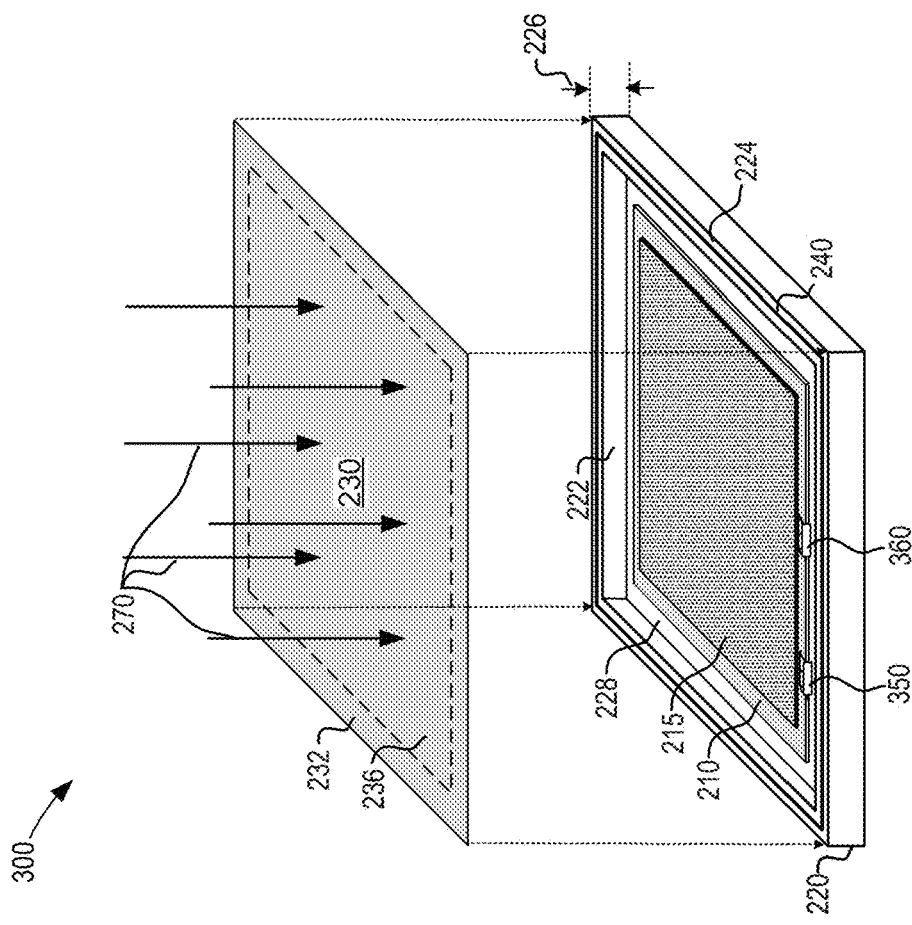

Turning now to FIGS. 3A and 3B, they illustrate an alternative embodiment of a wireless x-ray detector 300. In wireless x-ray detector 300, the electrical connector 250 is replaced by a wireless transmitter 350 and a wireless power connector 360. Wireless transmitter 350 and wireless power connector 360 facilitate transmission of digital signals and power, respectively, to and from the image sensor 210 wirelessly. As shown in FIG. 3A, a single wireless transmitter 350 and a single wireless power connector 360 are shown, however the number of those devices used may be more than one and their number may correspond to the amount and quality of digital signals and power that are wirelessly transmitted to and from the image sensor. For example, a greater number of wireless transmitters 350 may be used for faster transmission of a higher number of signals from the x-ray detector 300. Furthermore, a greater number of wireless power connectors 360 may be used for faster transmission of a larger amount of power to the x-ray detector 300. Accordingly, sealing of wireless x-ray detector 300 is simplified relative to x-ray detector 200 because wireless transmission of the digital signals and power to/from the image sensor 210 precludes having the electrical connector 250, resealable circumferential seal 256, and opening 260 in the raised flange 220. Similar to x-ray detector 200, wireless x-ray detector 300 is sealed around the perimeter of raised flange 220 when the cover 230 is attached to the raised flange 220 compressing seal 240 sandwiched therebetween. As described above, seal 240 may include a non-resealable seal or a resealable seal.

Wireless transmitter 350 may further include a wireless receiver so that signals indicating operating conditions of the x-ray detector 300 such as moisture, temperature, voltage, current, and the like, may be both wirelessly transmitted and received by the x-ray detector. Wireless signal transmission across the cover 230, flange 222, and bottom surface 228 of the housing may be achieved by various wireless electrical technologies, including but not limited to Wi-Fi, ultra-wide band (UWB), and other radio-wave based wireless communication technologies.

Furthermore, wireless signal transmission across the housing cover 230, flange 222, and bottom surface 228 may occur via optical transmission. In the case of optical transmission of signals through the housing, one or more of the cover 230, flange 222, and bottom surface 228 may comprise an optically transmissive material such as glass. Furthermore the optically transmissive material may comprise a portion of one or more of the cover 230, flange 222, and bottom surface 228. In one example, the optically transmissive material may comprise glass. In the case where the optically transmissive material cannot be semi-hermetically sealed, the portion of the housing forming the seal may comprise a non-optically transmissive material, so long as a fraction of the housing comprising optically transmissive material is high enough so that the transmission and reception of wireless signals and wireless power is not hindered and the performance of the x-ray detector is not reduced. Wireless power connector 360 may receive power wirelessly from a wireless power source external to the housing of the x-ray detector 300. The wireless power transfer across or through the housing may be accomplished by various wireless power technologies including but not limited to inductive coupling, capacitive coupling, and other wireless power technologies based on time-varying electric, magnetic, or electromagnetic fields. Accordingly, at least a portion of one or more of the cover 230, flange 222, and bottom surface 228 may comprise a material that is transmissive to one or more of the above-named wireless power transmission methods.

For example, the x-ray detector may include one or more inductive coils conductively coupled to a battery within the housing of the x-ray detector. Additionally, one or more inductive coils may be positioned in proximity to the x-ray detector, but external to the housing of the x-ray detector. Power via an alternating electromagnetic field generated from the inductive coils external to the housing may be transmitted wirelessly through one or more of the cover 230, flange 222, and bottom surface 228 of the housing to the one or more inductive coils within the housing. The inductive coils within the housing then convert the power from the electromagnetic field to electrical current, thereby inductively charging the battery.

Turning now to FIG. 4, it illustrates an embodiment of a wireless x-ray detector 400 comprising a multiply-tiled pixel array. In one example, x-ray detector 400 may include a CMOS x-ray detector having an image sensor panel comprising more than one pixel array. In the case of FIG. 4, the x-ray detector 400 includes an array of four pixel array tiles 480, 482, 484, and 486. Integrated with each of the pixel array tiles 480, 482, 484, and 486, are all the electronics in the CMOS sensor such as the wireless transmitters 350, wireless power connectors 360, and the scintillator 215, so that incident x-rays 270 into each of the pixel array tiles are converted to visible light photons, where they are sensed and received by the image sensors 210, and the corresponding digital signals are transmitted out of the housing via wireless transmitters 350. Power may be transferred wirelessly to one or more pixel array tiles 480, 482, 484, and 486 of the x-ray detector 400 from an external power source to wireless power connectors 360. Each of the pixel array tiles is conductively coupled to a wireless power connector 360 and a wireless transmitter 350 for wirelessly receiving and transmitting the wireless digital signals thereto and therefrom. Each of the pixel array tiles 480, 482, 484, and 486 may include a printed circuit board ("PCB") 490 conductively coupled to the image sensor 210. In the example of FIG. 4, the x-ray detector 400 includes four wireless transmitters 350 and four wireless power connectors 360 (each corresponding to an individual pixel array tile) for transmitting/receiving the digital signals and for receiving the wireless power, respectively. In other examples, there may be more than one wireless transmitter 350 supporting wireless communication to and from each pixel array tile. Furthermore, there may be more than one wireless power connector 360 supporting power supply to each pixel array tile.

Accordingly, sealing of wireless x-ray detector having multiple pixel array tiles is simplified relative to sealing x-ray detector 200 because wireless transmission of the digital signals and power to/from the image sensors 210 precludes having the electrical connectors 250, resealable circumferential seals 256, and openings 260 in the raised flange 220. Wireless x-ray detector 400 having multiple pixel array tiles is sealed around the perimeter of raised flange 220 when the cover 230 is attached to the raised flange 220 compressing seal 240 sandwiched therebetween.

Although the tiles of the pixel array are placed as close together as possible, abutting gaps 402 exist between the tiles. The abutting gaps 402 are vulnerable to trapping moisture that can degrade the scintillators 215 and the electronics inside the housing. Abutting gaps 402 are difficult to seal using conventional x-ray detector sealing methods such as thin films, coatings, and bonded sealants. By positioning the sealing surfaces of the x-ray detector 400 at the top surface 224 of the raised flange 220 and the sealing region 232 of the cover, away from and above the bottom surface 228 substrate and the surfaces in contact with the scintillators 215 and image sensors 210, the challenge of sealing the abutting gaps is averted, thereby simplifying and increasing a hermeticity of the sealing of the x-ray detector 400 including multiply-tiled pixel array image sensor, as compared to conventional methods.

Figure 5:
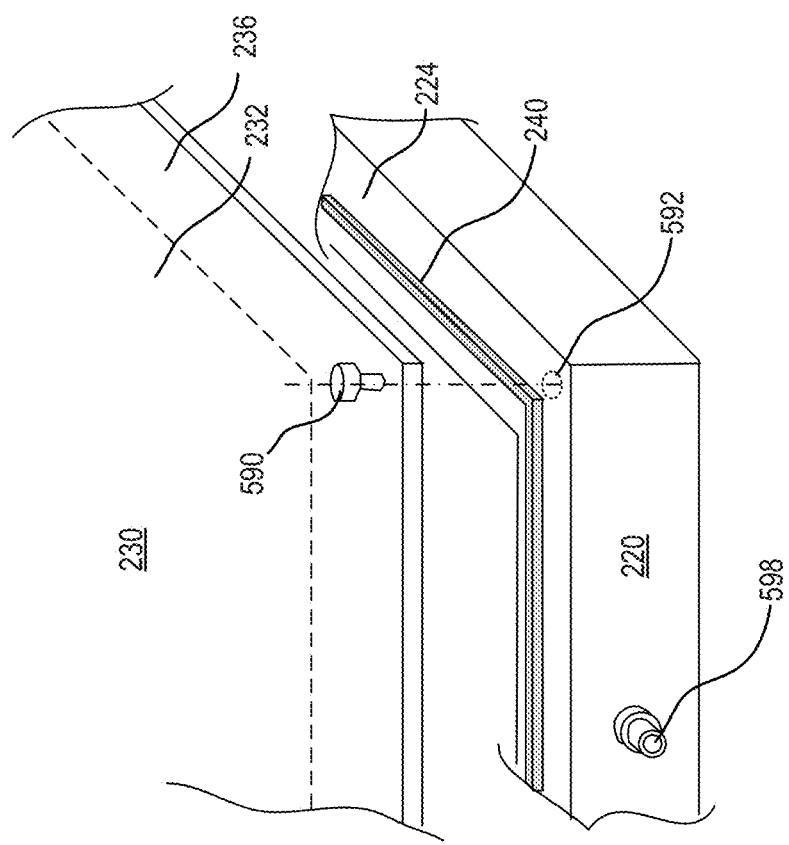
FIG. 5 is a schematic showing an enlarged partial perspective view of a wireless x-ray detector including a seal.

Turning now to FIG. 5, it illustrates an enlarged partially exploded perspective view of an x-ray detector 200. As shown in FIG. 5, x-ray detector 200 may further comprise one or more fasteners 590 and one or more fastener receiving structures 592 located in the housing. The fasteners 590 may comprise a screw, bolt, nail, rivet, bracket, strap or other type of mechanical fastener that can be used for attaching or removably attaching the cover 230 to the raised flange 220. The fastener receiving structures 592 may comprise a hole, hook, or other structure designed to firmly attach cover 230 to the raised flange 220 when fastener 590 is received by fastener receiving structure 590. The fastener receiving structures 592 may be integrated into both the cover 230 and the raised flange 220, where needed. For example, threaded holes may be formed in the cover 230 and the top surface 224 of the raised flange 220 for receiving a screw, rivet, or bolt used for fastening or removably fastening cover 230 to the raised flange 220. The fasteners 590 and fastener receiving structures 592 may be evenly spaced around the perimeter of the cover sealing region 232 and the raised flange 220 so that upon fastening the cover 230 to the raised flange 220, the seal 240 is adequately compressed around the entire perimeter of the sealing surfaces to (hermetically or semi-hermetically) seal the surfaces between the cover 230 and the raised flange 220. As described above the sealing region 232 may be thicker than the active region 236 of the cover 230 to impart increased structural rigidity to the cover 230 as it is fastened to the raised flange. Preserving rigidity of the cover 230 while fastening the cover 230 to the raised flange 220 can aid in evenly compressing the seal 240 around the perimeter of the housing, which can reduce a risk of moisture intrusion into the x-ray detector 200.

The x-ray detector 200 may also comprise one or more additional pluggable ports 598. The pluggable port 598 can aid in detecting leaks in the housing assembly of the x-ray detector. In one example, the sealed x-ray detector 200 can be filled with dry helium gas via the pluggable port 598, after which the pluggable port 598 is plugged. Helium sensors can then be utilized to determine if any helium gas has leaked from any of the x-ray detector seals (e.g., seal 240). The leak testing may also be conducted using other types of gases and gas sensors. Furthermore, the leak detection can also be performed by coating the outside of the seals with a liquid surfactant (e.g., dish soap and water, and the like).

Additionally, the interior of the sealed housing can be purged with dry nitrogen gas (or another dry inert gas) via the pluggable port 598 to displace any air (and moisture) therein. The pluggable port 598 may be sealed hermetically or semi-hermetically using an O-ring, gasket, epoxy, solder, rubber, polymer, or any sealing material now known or known in the future that will create a hermetic or semi-hermetic seal.

Turning now to FIGS. 6A-6D, they illustrate cross sectional views of several non-limiting example configurations of the seal 240 sandwiched between the cover 230 and the raised flange 220. A dotted line delineates the thicker sealing region 232 from thinner active region 236 of the cover 230. As discussed earlier, the increased thickness of the sealing region 232 around the perimeter of the cover 230 increases structural rigidity of the cover when attaching the cover 230 to the raised flange 220, which can aid in increasing seal hermeticity since the seal 240 is compressed more uniformly around the housing. Furthermore, reducing the thickness of the central active region 236 of the cover 230 can aid in increasing performance of the x-ray detector by reducing interference (e.g., absorption, deflection, and the like) with incident x-rays 270. Reducing the thickness of the active region 236 also reduces a weight of the x-ray detector, which can aid in improving the ergonomics and user-friendliness of the x-ray detector. The transition in thickness from the sealing region 232 to the active region 236 may be sharp, as shown for the example configurations of FIGS. 6A, 6B, and 6D, where the cover thickness abruptly changes at the boundary therebetween; alternately, as in the example configuration of FIG. 6C, the transition in thickness from the sealing region 232 to the active region 236 may be gradual, which can provide increased flexural strength to the cover, while reducing a weight of the cover.

Figure 6A:
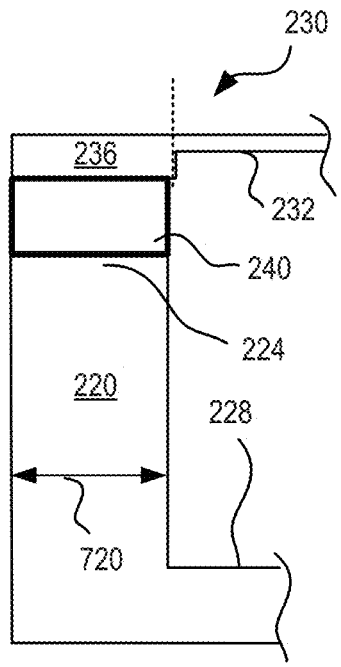
FIGS. 6A-6D are schematics showing enlarged cross-sectional views of seal configurations used in the x-ray detectors of FIGS. 2A, 2B, 3A, 3B, 4, 5, and 7.

As shown in FIG. 6A, the seal 240 may span a thickness 720 of the raised flange 220 and a thickness of the sealing region 232 of the top cover 230, and may be vertically sandwiched and compressed therebetween upon sealing the x-ray detector. The perimeter dimensions of the cover 230 match the perimeter dimensions of the raised flange 220, and hence when the cover is affixed to the raised flange 220, upon sealing the housing, an outer edge of the cover 230 is flush with the outer edge of the raised flange 220. A cross section of the seal 240 is shown as rectangular, however, as described above, circular, ovular, hollow, or other cross-sectional geometries may be possible. An advantage of the rectangular cross-section shown is that both sealing surfaces of the seal 240 fully span and contact the top surface 224 and the sealing region 232, which can enhance the hermeticity of the seal and reduce a risk of moisture intrusion into the x-ray detector. The thickness of the seal 240 in alternate examples may be less than the thickness 720 of the raised flange 220, but can still achieve a semi-hermetic or hermetic seal upon compression of the seal 240 between the cover 230 and the raised flange 220.

Figure 6B:
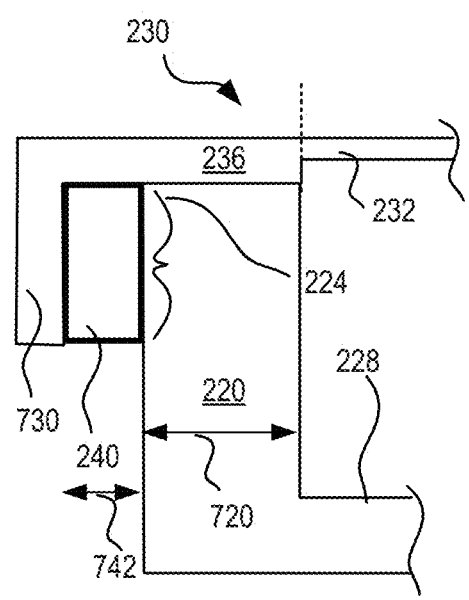

As shown in FIG. 6B, the cover 230 may overlap and overhang the outer edge of the raised flange 220, forming an overhanging lip 730. Accordingly, the seal 240 may be sandwiched between the overhanging lip 730 of the sealing region 232 of the cover 230 and a top surface 224 of the raised flange 220. Here, the top surface 224 includes a top surface of the outer edge of the raised flange 220. The thickness of the seal 240 may be formed slightly thicker than the thickness of the gap 742 formed between the overhanging lip 730 and the outer edge of the raised flange 220 so that when the cover 230 is attached to the raised flange 220, thereby horizontally compressing the seal 240, the hermeticity of the seal is increased and a risk of moisture intrusion is reduced. The configuration of sandwiching the seal 240 between the overhanging lip 730 and the outer edge of the raised flange 220 may be advantageous to increasing a hermeticity of the x-ray detector since the path length for moisture to diffuse through the seal is increased. For example, as shown in FIG. 6B, moisture must travel vertically upwards between the seal 240 and the overhanging lip 730 or between the seal 240 and the outer edge of the raised flange 220, and then across the thickness 720 of the raised flange 220 before reaching the interior of the housing.

Figure 6C:
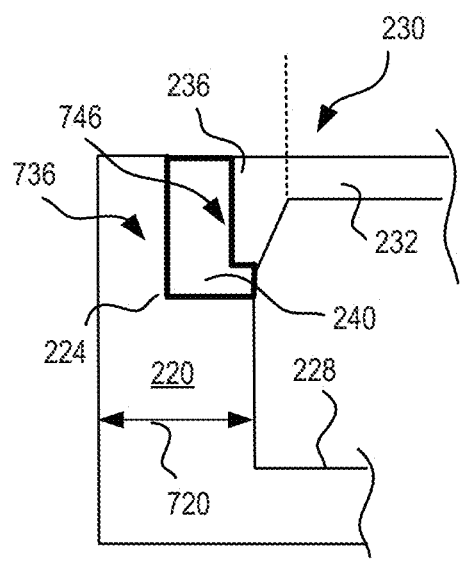

Turning now to FIG. 6C, it illustrates another example configuration of the seal 240, raised flange 220, and cover 230. Raised flange may be shaped to include a cutout 736 into the top surface 224 of the raised flange 220 contacting and forming a sealing surface with the seal 240. Similarly, the seal 240 may also be formed to include a cutout 746 into the surface of the seal 240 contacting and forming a sealing surface with the cover 230. Cutouts 736 and 746 serve to align and seat the seal 240 on the raised flange 220 and the cover 230 on the seal 240, respectively. In this way, the forming of the seal and the alignment of the opposing sealable surfaces between the seal 240 and the raised flange 220, and between the cover 230 and the seal 240, can be more reliably made each time the seal is resealed. Furthermore, the cutouts 736 and 746 also increase a distance and tortuosity that intruding moisture must travel in order to reach the housing interior, thereby increasing the seal hermeticity. As shown in FIG. 6C, the L-shaped cutouts 736 and 746 facilitate oblique (simultaneous horizontal and vertical) compression of the resealable seal when the cover 230 is fastened to the raised flange 220.

Figure 6D:
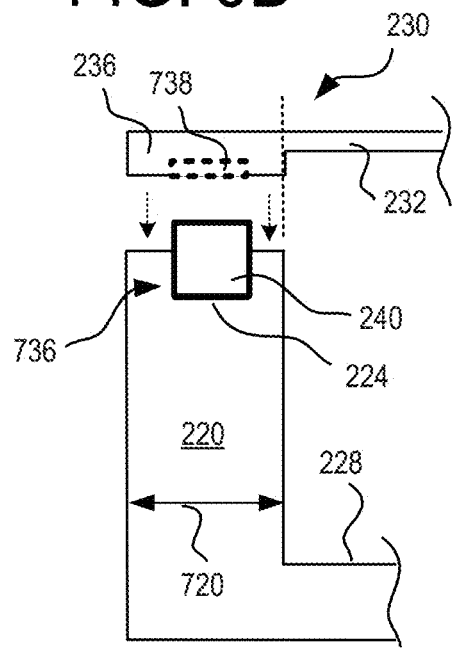

Turning now to FIG. 6D, it illustrates another example configuration of the seal 240, raised flange 220, and cover 230. Here, the top surface 224 of the raised flange comprises a cutout 736 facing the seal 240, and the cover 230 also includes a cutout 738 in the underside surface of the sealing region 232 facing the seal 240. As shown in FIG. 6D, the cutouts 736 and 738 may be shaped to, in combination, correspond to a cross-sectional geometry of the seal 240, and may be sized so that a combined cross-sectional area of the cutouts 736 and 738 may be slightly less than the cross-sectional area of the seal 240. In this way, upon fastening the cover 230 to the raised flange 220, the seal 240 may be compressed, thereby forming a seal therebetween with increased hermeticity. The cutouts 736 and 738 also increase a distance that intruding moisture must diffuse in order across the sealable surfaces (between the cover 230 and the seal 240, and between the seal 240 and the top surface 224 of the raised flange 220) to reach the interior of the housing. In FIG. 6D, the rectangular cross sectional geometries of the cutouts 736 and 738 and the seal 240 are exemplary and non-limiting, and any practical cross-sectional geometry may be used, such has circular, ovular, regular polygonal, irregular polygonal, and the like.

Turning now to FIG. 7, it illustrates an additional embodiment of an x-ray detector 200, including additional components placed in the housing interior. Positioning the sealing region, including the seal 240, the top surface 224 of the raised flange 220, and the sealing region 232 of the cover 230 apart and separated from the image sensor 210 and the scintillator 215 and the surfaces directly adjacent to and in contact therewith creates free volume within the housing in which additional components may be positioned. Because height 226 of the raised flange is greater than the height of the scintillator 215, image sensor 210, and bottom surface 228 combined, the sealing region is raised above a top surface of the scintillator 215 so that when the cover 230 is fastened to the top surface 224, there may be a space or gap between the top surface of the scintillator 215 and the undersurface of the cover 230. Furthermore, as shown in FIG. 7, the bottom surface 228 of the flanged base may be greater in one or more dimensions than the scintillator 215 and the image sensor 210 such that there may exist a perimeter region of the bottom surface 228 where additional components may be placed in housing. For example, getter material 810 for absorbing moisture or other substances may be placed at an interior surface within the housing.

The placement of the getter material may be concentrated at a particular location, as shown in FIG. 7 where the getter material 810 is placed in a corner of the bottom surface 228, or the getter material 810 may be distributed throughout interior surfaces of the housing. In one example, the getter material may be placed nearer to the sealing region, for example at the perimeter of the undersurface of the cover 230, or at the internal walls of the raised flange 220 near the interface with the fastened cover 230 to reduce a risk of moisture intrusion. In the case where the getter material is coated at the undersurface of the active region 236 of the cover, the getter material coating may be thin, of low density and non-absorptive towards the incident x-rays 270.

In another example, the getter material 810 may be placed nearer to the pluggable port 598 to reduce a risk of moisture intrusion. In another example, the getter material 810 may comprise a coating on one or more interior surfaces of the housing. As non-limiting examples, the getter material 810 may be coated at the underside of the cover 230, the interior walls of the raised flange 220, or along exposed areas of the bottom surface 228. The getter material 810 may further comprise sheets, strips, wires or sintered pellets of gas absorbing metals, or a paste applied to an interior housing surface. Moisture may preferentially be absorbed at the getter material 810 instead of the scintillator 215 or the image sensor (and other electronics components within the housing), thereby reducing a risk of x-ray detector degradation.

Furthermore, the getter material 810 may comprise an oxygen getter material to scavenge oxygen within the housing, for example, in the case of an x-ray panel detector comprising organic diodes. Oxygen getter material may comprise commercially available getter material from SAES group, Johnson Matthey, and the like. Further still, a shock absorption material can be used to protect the imager from damage inside the x-ray imager sealing housing. Shock absorption material comes in many forms including foam, solid, fibrous material and the like.

Various sensors 820 may also be positioned inside the x-ray detector housing, and may be conductively coupled to one or more of the image sensor 210, the scintillator 215, and the one or more wireless transmitters 350. In one embodiment, sensors 820 may include a moisture or humidity sensor for detecting moisture intrusion into the housing. The moisture sensor 820 may transmit a digital signal to an x-ray detector controller positioned external to the housing, and the controller, may execute a responsive controlling action. For example, in response to a moisture level in the housing being greater than a threshold moisture level, the controller may generate an audio and/or visual alarm indication, and may reduce or shut off a power supply to the x-ray detector in order to reduce a risk of degradation to the x-ray detector. In another embodiment, sensors 820 may include a temperature sensor, and the controller, in response to a temperature being greater than a threshold temperature, may generate an audio and/or visual alarm indication, and may reduce or shut off a power supply to the x-ray detector in order to reduce a risk of degradation to the x-ray detector. As another example, sensors 820 may include an oxygen sensor to detect intrusion of air or oxygen into the housing, indicating seal integrity degradation. In response to an oxygen level being greater than a threshold oxygen level, the controller may generate an audio and/or visual alarm indication, and may reduce or shut off a power supply to the x-ray detector in order to reduce a risk of degradation to the x-ray detector.

Turning now to FIG. 8, it illustrates a method 900 for assembling an x-ray detector. Method 900 begins at 910 where the x-ray imager, comprising the scintillator 215 and the image sensor 210 are positioned on the bottom surface 228 of an x-ray detector housing. As described above, the x-ray detector may include a plurality of pixel array tiles, each tile in the pixel array comprising its own scintillator and image sensor and separated from other tiles by abutting gaps 402 therebetween (as shown in FIG. 4). Furthermore, the housing may comprise a flanged base, the perimeter of the bottom surface 228 being surrounded by a raised flange 220 whose height 226 is greater than the top surface of the x-ray imager. As such, the seal 240 positioned the top surface 224 of the raised flange 220, is higher than the top surface of the x-ray imager. Further still, the dimensions of the bottom surface 228 may be greater than the dimensions of the x-ray imager so that there may be regions of the bottom surface 228 that are exposed and uncovered by the x-ray imager.

Next at 920, the getter material 810 may be positioned at an interior surface of the housing. The getter material may comprise a desiccant or other material that preferentially absorbs moisture (relative to the scintillator materials) and thus can aid in reducing a risk of degradation of the x-ray detector. The getter material may be coated on one or more interior surfaces of the housing, such as on the underside of the sealing region 232, the interior walls of the raised flange 220, or nearer to a pluggable port 598 in the housing. At 930, one or more sensors 820, such as a temperature and/or moisture sensor and/or oxygen sensor, may also be positioned inside the housing. The one or more sensors may be conductively coupled to the x-ray imager, and to one or more wireless transmitters 350 (see 950) for wirelessly transmitting the sensor output through the housing to a computer external to the housing.

Method 900 continues at 950 where one or more wireless transmitters 350 are positioned inside the housing and conductively coupled to the x-ray imager and sensor(s). In this way, hermeticity of the sealing of the x-ray detector housing may be increased relative to x-ray detectors receiving power from wired power supplies since the wired power connections are absent from the wirelessly powered x-ray detector and thus sealing around the wired power connections entering the housing is precluded. As described above, more than one wireless transmitter 350 may be positioned inside the housing and conductively coupled to the x-ray imager. The wireless transmitter 350 may be configured to transmit and receive wireless signal transmissions to and from a computer positioned external to the housing. The wireless transmitter 350 may further receive wirelessly transmitted digital signals to the x-ray imager and responsively actuate one or more electronic components within the housing. Furthermore, the external computer may, in response to a wireless digital signal received from the wireless transmitter 350, transmit one or more digital signals back to the wireless transmitter 350. In this way, sealing hermeticity of the x-ray detector housing may be increased relative to x-ray detectors receiving digital signals from wired electrical connections to computers and other components external to the housing since the wired electrical connections are absent from the wireless x-ray detector and thus sealing around the wired electrical connections entering the housing is precluded. In the case of the x-ray detector comprising plurality of pixel array tiles, each tile in the pixel array comprising its own scintillator and image sensor and separated from other tiles by abutting gaps 402 therebetween, one or more wireless transmitters 350 may be conductively coupled to each image sensor. For example, a larger number of wireless transmitters 350 may be conductively coupled to each x-ray imager inside the housing to increase a wireless signal transmission (and reception) rate and/or quality across the housing. Furthermore, in the case where a plurality of x-ray imagers are positioned inside the housing, one of the plurality of x-ray imagers may be conductively coupled to a different number of wireless transmitters 350 than another of the plurality of x-ray imagers.

Next, at 960, a wireless power connector 360 may be positioned inside the housing and conductively coupled to the x-ray imager. The wireless power connector 360 may be configured to receive wireless power transmission from a wireless power supply positioned external to the housing. The wireless power connector 360 may further supply the transmitted wireless power to the x-ray imager, sensors, and other electronic components within the housing. In this way, sealing of the x-ray detector housing may be improved relative to x-ray detectors receiving power from wired power supplies since the wired power connections are absent from the wirelessly powered x-ray detector and thus sealing around the wired power connections entering the housing is precluded. In the case of the x-ray detector comprising plurality of pixel array tiles, each tile in the pixel array comprising its own scintillator and image sensor and separated from other tiles by abutting gaps 402 therebetween, one or more wireless power connectors 360 may be conductively coupled to each image sensor. For example, a larger number of wireless power connectors 360 may be conductively coupled to each x-ray imager inside the housing to increase a wireless power transmission rate and/or quality across the housing. Furthermore, in the case where a plurality of x-ray imagers are positioned inside the housing, one of the plurality of x-ray imagers may be conductively coupled to a different number of wireless power connectors 360 than another of the plurality of x-ray imagers.

Following 960, method 900 continues at 970 where a seal 240 is positioned at a top surface 224 of the raised flange 220, thereby moving the sealing surfaces of the x-ray detector apart from the x-ray imager (e.g., the scintillator and the image sensor) and any surfaces directly adjacent thereto. The resealable seal is formed by removably fastening the cover 230 at the sealing region 232, on the top surface 224 of the raised flange 220. As described above with reference to FIG. 5, the cover can be fastened or removably fastened in various ways including being bolted, bracketed, riveted, screwed, and the like. At 980, after resealably sealing the x-ray detector, the housing may be purged with a dry inert gas through the pluggable port 598 to remove any moisture therein. Next, at 990, the pluggable port 598 may be plugged or removably plugged and a leak test may be performed to determine the hermeticity of the resealable seal between the cover 230 and the raised flange 220. After 990, method 900 ends.

Turning now to FIG. 9, it illustrates an example method 1000 for resealing an wireless x-ray detector system.

Method 1000 may comprise executable instructions on board a controller external to the housing that may executed by a computer processor in wireless communication with the x-ray detector. For example, the wireless x-ray detector may comprise one or more wireless transmitters 350 conductively coupled to the x-ray imager for transmitting and receiving digital signals to and from electrical components within the x-ray imager across the housing from and to an external computer. Furthermore, the wireless x-ray detector may comprise one or more wireless power connectors 360 conductively coupled to the x-ray imager for receiving wireless power from a power supply positioned external to the housing of the x-ray detector. Method 1000 begins at 1010 where the x-ray detector system operating conditions such as the temperature, oxygen level, and/or moisture inside the x-ray detector housing are wirelessly transmitted across the housing and received by a controller onboard a computer external to the housing. The controller may also receive operating conditions such as the wireless digital signal transmission rate and the wireless power transmission rate across the housing.

At 1020, the controller determines if one or more of the sensed operating conditions such as temperature, oxygen level, and/or moisture have exceeded or moved beyond a threshold condition. For example, as shown in FIG. 9, method 1000 determines if the moisture is greater than a threshold moisture, $Moisture_{TH}$. If $Moisture > Moisture_{TH}$, method 1000 continues at 1030, where the controller may wirelessly transmit a digital signal through the housing of the x-ray detector to generate an operator indication to warn the x-ray detector operator that a sensed condition has crossed a threshold level. The operator indication may comprise an audio and/or visual alarm, for example.

In another example, the controller at 1020 may determine if a wireless digital signal transmission rate or a wireless power transmission rate is below a threshold digital signal transmission rate or a threshold power transmission rate, respectively. If the wireless digital signal transmission rate is below a threshold digital signal transmission rate or if the wireless power transmission rate is below a threshold power transmission rate, method 1000 continues at 1030, where the controller may wirelessly transmit a digital signal through the housing of the x-ray detector to generate an operator indication to warn the x-ray detector operator that a sensed condition has crossed a threshold level. The operator indication may comprise an audio and/or visual alarm, for example.

At 1040, in response to the operator indication at 1030, the x-ray detector may be serviced. Servicing the x-ray detector may comprise opening the resealable seal between the cover 230 and the raised flange 220. After unsealing the x-ray detector, the x-ray imager and other components positioned inside the housing may be inspected, repaired, and/or replaced. For example, a faulty moisture sensor may be replaced, additional getter material may added to an interior surface of the housing, a seal 240 may be replaced, a wireless power connector 360 may be replaced or added, a wireless transmitter 350 may be replaced or added, and the like. Adding extra wireless transmitters 350 or replacing faulty wireless transmitters 350 may increase a wireless digital signal transmission rate across the housing, thereby increasing a performance of the x-ray detector. Adding extra wireless power connectors 360 or replacing faulty wireless power connectors 360 may increase a wireless power transmission rate across the housing, thereby increasing a performance of the x-ray detector.

At 1040, in the case of a wireless power transmission rate being below a threshold power transmission rate, servicing the x-ray detector may comprise increasing a power transmission from the external power supply to the x-ray detector. In the case where increasing the power transmission from the external power supply to the x-ray detector increases the wireless power transmission rate above the threshold power transmission rate, unsealing the x-ray detector at 1040 may be precluded.

After servicing the detector at 1040 method 1000 continues at 1046 where it is determined if the x-ray detector needs resealing after servicing. For example, as just described above for 1040, in the case where increasing the power transmission from the external power supply to the x-ray detector increases the wireless power transmission rate above the threshold power transmission rate, unsealing the x-ray detector at 1040 may be precluded, and thus the x-ray detector remains sealed and is not resealed after servicing at 1046. For the case where the x-ray detector is not resealed after servicing at 1046, method 1000 ends. Conversely, for the case where servicing the x-ray detector comprises replacing or adding one or more components such as sensors, getter material, wireless power connectors, and/or wireless power transmitters to the x-ray detector, the x-ray detector is resealed after servicing at 1046.

For the case where the x-ray detector is resealed after servicing at 1046, method 1000 continues at 1050 where the x-ray detector may be resealed by positioning the seal 240 at the top surface 224 of the raised flange 220 and fastening or removably fastening the cover on the top surface of the raised flange, respectively. Similar to steps 980 and 990 of method 900, after resealably sealing the x-ray detector at 1050, method 1000 may continue at steps 1060 and 1070 where the housing is purged with a dry inert gas and leak testing is performed. After 1070 and at 1020 when $Moisture < Moisture_{TH}$ (or an operating condition no longer is beyond the threshold operating condition) method 1000 ends.

As provided above, scintillator sealing for solid state x-ray detectors is shown and described. In one embodiment, an x-ray detector is provided including a housing, including a cover fastened on a flange of a flanged base and forming a seal therebetween, the flanged base including a bottom surface and the flange surrounding a perimeter of the bottom surface and an x-ray imager positioned on the bottom surface, the x-ray imager including a wireless transmitter. The seal may semi-hermetically enclose the x-ray imager in the housing, and may be positioned nonadjacently to surfaces in contact with the x-ray imager. In some examples, in the absence of the seal between the cover and the flanged base, the semi-hermeticity of the x-ray imager may be lost. Further, in some examples, a semi-hermetically resealable material sandwiched between the cover and the flange and surrounding the perimeter the bottom surface may be provided. The wireless transmitter may comprise a wireless optical transmitter, and one of the flange, the bottom surface, and the cover may comprise an optically transmissive material. In some examples the optically transmissive material may include a fiber optic cable, and the x-ray imager may further comprise a wireless power connector. In one example, the wireless power connector may comprise an inductively charged battery.

An x-ray imaging system is also provided including a housing, including a cover fastened on a raised flange of a flanged base thereby forming a seal therebetween, an x-ray imager positioned on a bottom surface of the flanged base inside the housing below and nonadjacent to the seal, the raised flange surrounding a perimeter of the bottom surface. The seal may comprise a resealable seal, and the x-ray imaging system may further include a wireless transmitter positioned inside the housing and conductively coupled to the x-ray imager, and a wireless power source positioned external to the housing. The x-ray imaging system may further comprise a wireless power connector positioned inside the housing and conductively coupled to the x-ray imager, and the wireless power source may receive wireless energy transmission from the wireless power source.

The x-ray imaging system may further comprise a controller external to the housing, the controller may be conductively coupled to the wireless power source, and the controller may receive wireless energy transmissions from the wireless transmitter. In some examples, the controller may include executable instructions stored thereon to, in response to a signal from the wireless transmitter indicating a power level less than a threshold power level, increase a wireless power transmission rate from the wireless power source to the wireless power connector. Furthermore, the x-ray imaging system may comprise a moisture sensor positioned in the housing and conductively coupled to the wireless transmitter, and the controller may include executable instructions stored thereon to, in response to a signal from the moisture sensor via the wireless transmitter indicating a moisture level above a threshold moisture level, generate an indication to repair the x-ray imager.

A method of assembling an x-ray detector is provided, the x-ray detector including an x-ray imager, a housing, and a wireless transmitter. The method may include positioning the x-ray imager on a bottom surface of the housing, and the housing may include a cover and a raised flange surrounding a perimeter of the bottom surface. Additionally, the method may include positioning the wireless transmitter inside the housing and conductively coupling the wireless transmitter to the x-ray imager. The method may further include sealing the x-ray imager within the housing, including affixing the cover on a top surface of the raised flange to form a seal between the cover and the raised flange, and the seal may be positioned outside of a path of x-rays incident at the x-ray imager. The method may further include positioning a wireless power connector inside the housing, the wireless power connector conductively coupled to the x-ray imager.

In some examples, sealing the x-ray imager further comprises sandwiching a reusable sealing material between the cover and the raised flange. Furthermore, the method may include placing getter material at an interior surface of the housing, and positioning a moisture sensor at an interior surface of the housing. Additionally, the method may include positioning the x-ray imager on the bottom surface of the housing, wherein one of the flange and the bottom surface include an optically transmissive material.

In this way, the technical effect of providing a seal for a digital x-ray panel in a simple, low cost way can be achieved. Further technical effects are listed as follows. In the case where the seal is reusable and resealable, the technical effect of enabling repair and refurbishment of the device is facilitated. Further still, the seal is positioned away from the detector-active region and thus does not interfere with the detector operation, and reduces a risk of damaging the detector components during manufacturing. Further still, positioning the seal away from the detector-active region can facilitate addition of other components within the x-ray detector housing such as getter material, sensors, electrical connectors, and the like, which can increase the performance and functionality of the x-ray detector. Further still, the seal facilitates sealing multiply-tiled large image array detectors within a single x-ray detector. Further still, the seal may comprise a semi-hermetic seal or a hermetic seal. Further still, the hermeticity of the sealing of the x-ray panel is increased because transmission of power and other digital signals across the housing of the x-ray panel is performed wirelessly and sealing around wired connectors entering the housing is precluded.

It is to be understood that the description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to those of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Additionally, the term pixel is used throughout the specification and should be interpreted to include one or more pixel. The term pixel is not restricted by any number because of the use of singular or multiple form.

This written description uses examples to disclose several embodiments of the inventive subject matter and also to enable any person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

The invention claimed is:

1. An x-ray detector, comprising:
a housing, including a removable cover fastened on a flange of a flanged base and forming a seal therebetween, the flanged base including a bottom surface and the flange surrounding a perimeter of the bottom surface;
an x-ray imager positioned on the bottom surface, the x-ray imager including a wireless transmitter;
a wireless power source positioned external to the housing; and
a controller external to the housing, the controller conductively coupled to the wireless power source, the controller receiving wireless energy transmissions from the wireless transmitter,
wherein the seal semi-hermetically encloses the x-ray imager in the housing, and is positioned nonadjacently to surfaces in contact with the x-ray imager,
wherein one or more fastener receiving structures are integrated into the removable cover and the flange, and
wherein the removable cover is rigidly fixed to the flange via one or more fasteners being respectively received by the one or more fastener receiving structures.

2. The x-ray detector of claim 1, wherein the seal comprises a semi-hermetically resealable material sandwiched between the removable cover and the flange and surrounding the perimeter of the bottom surface.

3. The x-ray detector of claim 1, wherein the wireless transmitter comprises an optical wireless transmitter.

4. The x-ray detector of claim 1, wherein one of the flange, the bottom surface, and the removable cover comprises an optically transmissive material.

5. The x-ray detector of claim 4, wherein the optically transmissive material includes a fiber optic cable.

6. The x-ray detector of claim 1, wherein the x-ray imager further comprises a wireless power connector.

7. The x-ray detector of claim 6, wherein the wireless power connector comprises an inductively charged battery.

8. An x-ray imaging system, comprising:
a housing, including a removable cover fastened on a raised flange of a flanged base, thereby forming a seal therebetween;
an x-ray imager positioned on a bottom surface of the flanged base inside the housing below and nonadjacent to the seal, the raised flange surrounding a perimeter of the bottom surface;
a wireless transmitter positioned inside the housing and conductively coupled to the x-ray imager;
a moisture sensor positioned in the housing and conductively coupled to the wireless transmitter;
a wireless power source positioned external to the housing; and
a controller external to the housing, the controller conductively coupled to the wireless power source, the controller receiving wireless energy transmissions from the wireless transmitter.

9. The x-ray imaging system of claim 8, further comprising a wireless power connector positioned inside the housing and conductively coupled to the x-ray imager, the wireless power connector receiving wireless energy transmissions from the wireless power source.

10. The x-ray imaging system of claim 8, wherein the seal comprises a resealable seal.

11. The x-ray imaging system of claim 8, wherein the controller includes executable instructions stored thereon to, in response to a signal from the wireless transmitter indicating a power level less than a threshold power level, increase a wireless power transmission rate from the wireless power source to the wireless power connector.

12. The x-ray imaging system of claim 8, wherein the controller includes executable instructions stored thereon to, in response to a signal from the moisture sensor via the wireless transmitter indicating a moisture level above a threshold moisture level, generate an indication to repair the x-ray imager.

13. A method of assembling an x-ray detector including an x-ray imager, a housing, and a wireless transmitter, comprising:
positioning the x-ray imager on a bottom surface of the housing, the housing comprising a removable cover and a raised flange surrounding a perimeter of the bottom surface;
positioning a moisture sensor at an interior surface of the housing;
positioning the wireless transmitter inside the housing and conductively coupling the wireless transmitter to the x-ray imager; and
sealing the x-ray imager within the housing, including affixing the removable cover on a top surface of the raised flange to form a seal between the removable cover and the raised flange, wherein the seal is positioned outside of a path of x-rays incident at the x-ray imager.

14. The method of claim 13, further comprising positioning a wireless power connector inside the housing, the wireless power connector conductively coupled to the x-ray imager.

15. The method of claim 13, wherein sealing the x-ray imager further comprises sandwiching a reusable sealing material between the removable cover and the raised flange.

16. The method of claim 13, further comprising placing getter material at the interior surface of the housing.

17. The method of claim 13, further comprising positioning the x-ray imager on the bottom surface of the housing, wherein one of the raised flange and the bottom surface comprises an optically transmissive material.

18. The x-ray imaging system of claim 8, further comprising one or more pluggable ports.

19. The x-ray imaging system of claim 8, further comprising getter material positioned in the housing.

20. The method of claim 16, wherein placing the getter material comprises placing the getter material nearer to a pluggable port in the housing.

\* \* \* \* \*